(12) United States Patent
Costantino et al.

(10) Patent No.: US 12,397,096 B2
(45) Date of Patent: Aug. 26, 2025

(54) RED BLOOD CELLS FOR DRUG DELIVERY

(71) Applicant: POLITECNICO DI MILANO, Milan (IT)

(72) Inventors: Maria Laura Costantino, Milan (IT); Giustina Casagrande, Milan (IT); Monica Piergiovanni, Milan (IT); Elena Bianchi, Milan (IT); Clara Bernardelli, Milan (IT)

(73) Assignee: POLITECNICO DI MILANO, Milan (IT)

( * ) Notice: Subject to any disclaimer, the term of this patent is extended or adjusted under 35 U.S.C. 154(b) by 810 days.

(21) Appl. No.: 17/619,411

(22) PCT Filed: Jun. 19, 2020

(86) PCT No.: PCT/IB2020/055783
§ 371 (c)(1),
(2) Date: Dec. 15, 2021

(87) PCT Pub. No.: WO2020/255060
PCT Pub. Date: Dec. 24, 2020

(65) Prior Publication Data
US 2022/0257844 A1    Aug. 18, 2022

(30) Foreign Application Priority Data
Jun. 21, 2019   (IT) .................. 102019000009831

(51) Int. Cl.
*A61M 1/30*    (2006.01)
*A01N 1/02*    (2006.01)
(Continued)

(52) U.S. Cl.
CPC ............. *A61M 1/303* (2014.02); *A01N 1/146* (2025.01); *A61M 1/0209* (2013.01);
(Continued)

(58) Field of Classification Search
CPC .. A61M 1/303; A61M 1/0209; A61M 1/0272; A61M 1/308; A61M 1/3696;
(Continued)

(56) References Cited

U.S. PATENT DOCUMENTS 6,074,605 A * 6/2000 Meserol ................. C12M 35/02
435/173.6
2008/0102478 A1  5/2008 Li et al.
(Continued)

FOREIGN PATENT DOCUMENTS

WO    WO 2008/040015 A2    4/2008
WO    WO-2017008063 A1 *  1/2017  ............. A61K 35/18
(Continued)

OTHER PUBLICATIONS

Phosphate-Buffered Saline (PBS), 2006, Cold Spring Harbor Protocols (Year: 2006).*
(Continued)

*Primary Examiner* — Nicholas J. Weiss
*Assistant Examiner* — Brandon W. Levy
(74) *Attorney, Agent, or Firm* — Oblon, McClelland, Maier & Neustadt, L.L.P.

(57) ABSTRACT

It is an object of the present invention a method to introduce compounds inside red blood cells comprising: —providing red blood cells from a subject; —providing one or more compounds to be encapsulated in said red blood cells; —providing a loading device comprising a microporous matrix; —feeding said loading device with a suspension comprising said red blood cells and said one or more compounds; —collecting the red blood cells exiting from said loading device, which are encapsulated red blood cells; characterized in that: —said red blood cells and said one or more compound are in suspension at a pH of between 6.8 and 7.8, preferably of between 7.35 and 7.45; —the pores in
(Continued)

said microporous matrix have a minimum size of at least 3 times the size of a red blood cell, that is a minimum size of at least 20 µm; —the pores in said microporous matrix have an average size of between 30 and 500 µm, or of between 40 and 400 µm, or of between 50 and 350 µm, or of between 100 and 250 µm; —said porous matrix has a length L of at least 1 mm and a width W and a height H such that it comprises at least one unit cell, said unit cell being equal to the microporous matrix volume that, repeated by rototranslation through the vectors that generate the matrix, fills the whole matrix itself; wherein said loading device is fed with said suspension in such a way to obtain an average fluid speed of between $10^{-4}$ and 10 m/s. Further objects of the present invention are a microporous matrix, a loading device comprising the same, a fluidic circuit and a machine for implementing said method and red blood cells encapsulated with at least one compound according to said method.

9 Claims, 8 Drawing Sheets

(51) Int. Cl.
*A01N 1/146* (2025.01)
*A61M 1/02* (2006.01)
*A61M 1/36* (2006.01)
*C12N 5/078* (2010.01)

(52) U.S. Cl.
CPC .......... *A61M 1/0272* (2013.01); *A61M 1/308* (2014.02); *A61M 1/3696* (2014.02); *C12N 5/0641* (2013.01); *A61M 2202/0429* (2013.01)

(58) Field of Classification Search
CPC ........ A61M 2202/0429; A61M 1/3687; A61M 1/362266; A61M 2202/0057; A61M 2202/0092; A01N 1/146; C12N 5/0641; C12N 5/0644; C12M 35/04; C12M 23/16; C12M 35/02; A61K 35/18; A61K 9/5068; A61K 2300/00; A61K 38/42; A61K 9/0019; A61K 38/00; A61P 7/00; B01L 2400/0487; B01L 3/5027
See application file for complete search history.

(56) References Cited

U.S. PATENT DOCUMENTS

| | | |
|---|---|---|
| 2012/0070878 A1 | 3/2012 | Fink et al. |
| 2018/0201889 A1* | 7/2018 | Sharei .................... A61K 35/18 |
| 2019/0382796 A1 | 12/2019 | Gilbert et al. |

FOREIGN PATENT DOCUMENTS

| | | |
|---|---|---|
| WO | WO 2017/041050 A1 | 3/2017 |
| WO | WO 2017/123663 A1 | 7/2017 |
| WO | WO 2019/123372 A1 | 6/2019 |

OTHER PUBLICATIONS

Chi-Yuan Hsu, David W. Bates, Gilad J. Kuperman, Gary C. Curhan, Relationship between hematocrit and renal function in men and women, 2001, Kidney International, vol. 59, pp. 725-731 (Year: 2001).*

Casagrande et al. Application of Controlled Shear Stress on the Erythrocyte Membrane as a New Approach to Promote Molecule Encapsulation, 2016 Artificial Organs, vol. 40, No. 10, pp. 959-970. (Year: 2016).*

International Search Report issued Sep. 23, 2020 in PCT/IB2020/055783, citing documents AA—AD, AL—AO and AU—AW therein, 4 pages.

Giustina Casagrande, et al., "Application of Controlled Shear Stresses on the Erythrocyte Membrane as a New Approach to Promote Molecule Encapsulation: Erythrocyte Carriers" Artificial Organs, vol. 40, No. 10, XP055681574, Oct. 1, 2016, pp. 959-970.

Armon Sharei, et al., "Ex Vivo Cytosolic Delivery of Functional Macromolecules to Immune Cells" PLOS ONE, vol. 10, No. 4, XP055353029, Apr. 13, 2015, p. e0118803, pp. 1-12.

Monica Piergiovanni, et al., "Shear-Induced Encapsulation into Red Blood Cells: A New Microfluidic Approach to Drug Delivery" Annals of Biomedical Engineering, vol. 48, No. 1, XP036968962, Aug. 13, 2019, pp. 236-246.

W. Tillmann, et al., "In-Vitro Wall Shear Measurements at Aortic Valve Prostheses" Journal of Biomechanics, vol. 17, No. 4, 1984, pp. 263-279.

* cited by examiner

RED BLOOD CELLS FOR DRUG DELIVERY

FIELD OF INVENTION

Herein disclosed is a method to introduce at least one compound inside red blood cells, a loading device comprising a microporous matrix, a fluidic circuit and a machine for implementing said method and encapsulated red blood cells according to the methodology disclosed herein.

BACKGROUND OF THE INVENTION

Loading of drugs inside cells, in particular inside red blood cells, is a key step in the research and development of new therapies.

Known technologies aiming at intracellular delivery of compounds are based on electrical fields, nanoparticles or chemicals inducing pore formation in cell membranes allowing a compound to enter the intracellular region. Such a methodology is usually defined "encapsulation" and cells treated in such a way are defined "encapsulated". However, these methods suffer from several drawbacks, among which modification or damaging of the compounds to be delivered, high mortality of carrier cells, contact with potentially toxic materials, low efficiency.

As an example, WO2017041050 discloses a cell loading system mediated by the forced passage of said cells through pores of a diameter smaller than the diameter of the same cells.

WO2017008063 discloses a microfluidic channel having a constraint with a lumen smaller than 4 micrometres, and in any case never higher than 90% of the dimension of the cell used. Cells are made to pass through said channel creating a deformation on their wall, due to the contact with said constraint of the microfluidi channel, favouring the entry of material of interest inside the cells. To operate, the required pressure at the entry of the device is necessarily higher than 90 Psi, i.e. 6.1 atm.

Also WO2017123663 discloses a cell loading method, wherein said method is based on the passage of said cells in a constraint that deforms them in such a way to allow molecules of interest to enter inside them.

In Artif Organs 2016, 40(10): 959-970, Casagrande G. et al. disclose a methodology based on the passage of a suspension that includes the cells to be loaded and the compound in a long glass capillary tube. The obtained results show low loading efficiency, together with a high number of echinocyte indicating cell alteration exerted by the methodology itself, which therefore is not applicable in clinical practice.

The need for the provision of a methodology for loading compounds into cells is strongly felt, wherein the microfluidic methodology may handle flow rates such that it can be integrated in a microfluidic circuit even in the specific case of biomedical use.

DESCRIPTION OF THE INVENTION

It is an object of the present invention a method to introduce compounds inside one or more red blood cells, wherein said method is based on fluid dynamic and diffusion phenomena, which, under controlled chemical-physical conditions, surprisingly lead to the temporary opening of the pores on the cell membrane surface of red blood cells through which said compounds, added to the cell suspension, diffuse inside the red blood cells.

It is a further object of the present invention a fluidic circuit comprising a microporous matrix for implementing said method.

DETAILED DESCRIPTION OF THE INVENTION

Figure 1:
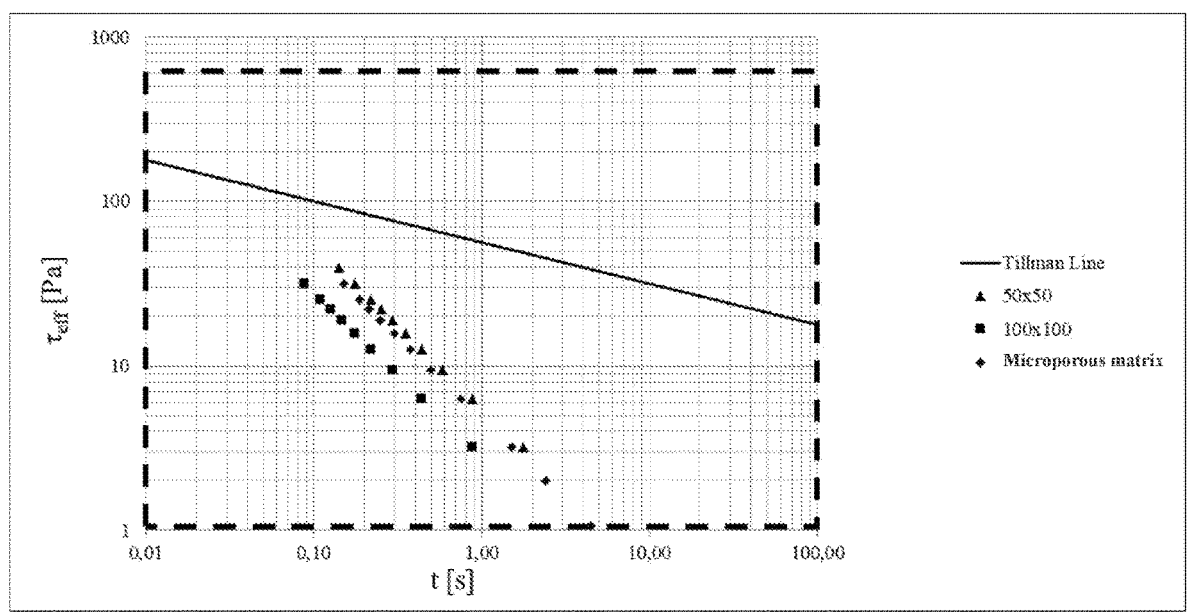
FIG. 1: a graph showing, in logarithmic scale, the relation between the stress acting on the red blood cell membrane and the time during which such a stress occurs. The highlighted rectangular area indicates the region satisfying the conditions according to the methodology of the present invention.

Definitions:

For the purposes of the present description, where not otherwise indicated, the terms used are to be understood as having the following meaning:

The term "compounds" means all those materials that the expert in the field intends to introduce, to encapsulate, in a red blood cell. As a non-exhaustive example compounds are small molecules, peptides, nucleic acids.

The term "encapsulated red blood cells" or "encapsulated blood" herein means red blood cells loaded with one or more compounds, or blood of which red blood cells are loaded with one or more compounds.

The term "microporous matrix" herein means a solid matrix crossed by an interconnected network of voids (pores) through which the presence and movement of a fluid is possible. Said interconnected network of pores generates interconnected fluidic channels characterized by minimum sections of dimensions defined by height parameters HC1, HC2 and width parameters WC1, WC2.

The term "porosity/porosities" indicates the pores dimension and shape.

Said microporous matrix has homogeneous and heterogeneous porosities, optionally said matrix has porosities placed in a preferential manner, so as to direct the flow in a preferential direction. Alternatively, said flow is directed confining said matrix in a suitable housing.

Said microporous matrix is characterized by cavities interconnected with each other and connected with the outside, so as to define a passage of fluid from an inlet surface to an outlet surface, through the cavities of the matrix. The size of the section normal to the main direction of the flow must be large enough (the dimensions H and W in the case of a rectangular section, or D diameter in the case of a circular section) to allow the fluid to follow even transversal paths, defined by the tortuosity cavity characteristics. The alternation of solids and voids is generated by arranging in the space solid elements such as fibers, spheres, spheroids or any other element of homogeneous or heterogeneous shape and material and exploiting cavities not filled by the aforementioned elements as 'voids'.

In a further embodiment, said microporous matrix is characterized by cavities generated by the presence of gas or a second liquid or solid material, removed during the production phase of the device. In this embodiment, said microporous matrix is similar to a foam.

In a further embodiment, the microporous matrix consists of capillaries/tubes characterized by having at least a porous portion of a wall, for example by concentric channels, characterized by at least partially porous walls, or by channels with at least partially porous surface, arranged in space so that the fluid can flow into a channel and pass outside it or inside another, through suitable pores on the walls.

Said microporous matrix is obtained via methodologies known to the expert in the field. As an example, it is obtained via solvent evaporation/particles release, fiber bonding, gas foaming, emulsion/freeze-frying, phase separation, 3D printing, electrospinning.

The term "unit cell" is intended to refer to the microporous matrix volume that, repeated by rototranslation through the vectors that generate the matrix, fills the whole matrix itself, i.e. the smallest part of said matrix that, repeated through the space, makes up the whole matrix.

Said unit cell forms a fluidic channel having a minimum height defined by HC1 and HC2 parameters, and minimum widths defined by WC1 and WC2 parameters, wherein said thicknesses HC1 and HC2 are equal or different each other and said widths WC1 and WC2 are equal or different each other. One unit cell, repeated through the space, originates the whole microporous matrix.

In one embodiment, the microporous matrix consists of repeating equal unit cells, in other embodiments, the microporous matrix is a set of microporous matrices, wherein each matrix making up the set of matrices consists of unit cells, said unit cells being equal or different between the different matrices that make up the set.

The term "polymeric material" comprises, but is not limited to, homopolymers, copolymers, such as, for example, blocks, grafts, random and alternate copolymers, terpolymers, and their mixtures and modifications. Furthermore, unless specifically limited otherwise, the term "polymer" also includes all possible geometric configurations of the molecule. These configurations include, among other things, isotactic, syndiotactic, atactic and random symmetries.

It is a first object of the present invention a method to introduce compounds inside red blood cells.

Said method comprises:

providing red blood cells from a subject;

providing one or more compounds to be encapsulated in said red blood cells;

providing a loading device comprising a microporous matrix;

feeding said loading device with a suspension comprising said red blood cells and said one or more compounds;

collecting the red blood cells exiting from said loading device, which are encapsulated red blood cells;

characterized in that:

said red blood cells and said one or more compound are in suspension at a pH of between 6.8 and 7.8, preferably of between 7.35 and 7.45;

the pores in said microporous matrix have a minimum size of at least 3 times the size of a red blood cell, i.e. a minimum size of at least 20 µm;

the pores in said microporous matrix have an average size of between 30 and 500 µm, or of between 40 and 400 µm, or of between 50 and 350 µm, or of between 100 and 250 µm;

said porous matrix has a length L of at least 1 mm, or at least 5 mm, and a width and a height such that it comprises at least one unit cell;

wherein said loading device is fed with said suspension in such a way to obtain an average fluid speed of between $10^{-4}$ and 10 m/s.

Said microporous matrix is made of polymeric material, and/or ceramic material and/or metallic material. In a further embodiment, said microporous matrix is a gel and/or a biological material, for example it is a decellularized matrix.

In a preferred embodiment, said microporous matrix has a length L of between 5 and 1000 mm, preferably between 6 and 500 mm, or between 8 and 300 mm or between 100 e 200 mm. Preferably, said microporous membrane has a height H equal to 2-1000 times, or 10-500 times, the height HU of the unit cell of which it is composed and/or a width W equal to 2-1000 times, or 10-500 times, the width WU of said unit cell.

Said loading device comprises a microporous matrix suitably housed in an housing which does not allow blood leakage between the porous medium and the housing itself and an inlet port and an outlet port. In an embodiment, said inlet port and outlet port are placed at the two longitudinal ends of said microporous matrix.

Figure 2A:
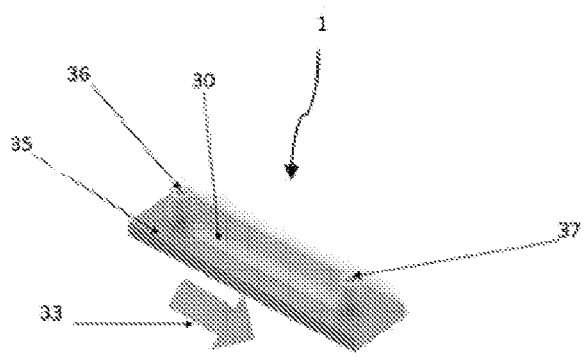
FIG. 2: (A) prospective view of a loading device wherein a microporous matrix is housed according to one embodiment; (B) prospective view of a portion of a microporous matrix according to one embodiment; (C) enlarged schematic prospective view of a unit cell; (D) prospective view from above of a portion of said microporous matrix inside the loading device.

With reference to the picture of FIG. 2A, the microporous matrix 30 is housed in an housing 35 of the loading device 1 having an inlet port 36 and an outlet port 37, wherein said loading device 1, when a fluid passes through it, sees a flow directed in the direction indicated by the arrow 33. In a further embodiment, said loading device further comprises a duct having a length and a section described by dimensions w and h, wherein said length is between 5 and 5000 mm, preferably between 5 and 500 mm, preferably between 40 and 200 mm, even more preferably between 40 and 130 mm, even more preferably of at least 60 mm and wherein said section has dimensions related to the microporous matrix dimensions, without ever narrowing below 20 μm, wherein said duct has a connecting and/or transporting function of said suspension to/from said matrix. Said section has dimension such that the smaller dimension among w and h of said section is higher than 20 μm, for example is between about 20 μm and 5000 mm, or between about 20 μm and 500 mm, or between 20 μm and 50 mm, or between 20 μm and 5 mm, or between 20 μm and 500 μm, or between 30 μm and 200 μm. In a preferred embodiment said section is constant along said duct, in alternative embodiments, said section varies along the duct, without however ever narrowing below 20 μm. In a further embodiment, said device comprises a first matrix portion linked through said duct to a second or further matrix portion.

Said average fluid speed is obtained with an inlet flow rate sufficiently high to avoid deposition of red blood cells in the loading device.

The hematocrit of said suspension is between 1 and 50%. In one embodiment, said suspension is obtained in PBS, obtaining a hematocrit of about 1%, or of about 5%. In alternative embodiments, the hematocrit of said suspension is between 25 and 40%.

Preferably, albumin is added to said PBS in order to preserve in the suspension the physiological albumin levels in the blood, equal to about 5 g/dl.

Alternatively, said suspension further comprises an anti-coagulant, for example CPD and/or a preservative, for example mannitol.

In a further embodiment, said red blood cells suspension is whole blood.

Preferably said subject is a mammal, in one embodiment it is a human. In one embodiment, said subject is a donor. In an alternative embodiment, said subject is the same patient in need of encapsulated red blood cells.

The authors of the present invention have surprisingly demonstrated that, working with the methodology object of the present invention, red blood cells undergo a stress field such that on their membrane it is possible to see the opening of transient pores for a time sufficient to encapsulate the compounds of interest. At the same time, said stress field does not affect the viability of the red blood cells, which, after loading, show an optimal viability and preservation of the characteristic biconcave shape. Such stresses are defined as sub-hemolytic. The microporous matrix solution disclosed herein allows the processing of blood volumes in a unit of time such as to make it suitable for clinical applications. As an example, the method according to the present invention allows to encapsulate with a high efficiency a volume of blood equal to about 1 L in an hour.

Said stress field is generated by the shear stress Tau (τ), in the particular case of laminar motions in circular ducts it is for example possible to approximate it with formula (1) and it is measured in Pascal, Pa=kg/(m*s$^2$).

$$\tau = 4\mu Q/(\mu r_i^3) \quad (1)$$

wherein μ is the fluid viscosity, Q the flow rate, and $r_i$ the internal radius of the cylindrical duct.

The persistence over time of said shear stress above a minimum time value ($t_{min}$), allows a "stress accumulation" (SA) sufficient to allow formation of temporary porosity on the red blood cells membrane.

These porosities are reversible if the stress ceases within a maximum time ($t_{MAX}$). $t_{min}$ and $t_{MAX}$ vary based on the mechanical characteristics of each individual's red blood cells. Diagrams are available in the literature that statistically show the probability of hemolysis based on the stress conditions (tau) and the persistence of the same stress (t).

As an example, in the graph in FIG. 1, the straight line τ=f(t) represents the shear stress τ over time, as proposed by Tillmann W et al., J Biomechanics 1984, 17: 263-279. In the same graph of FIG. 1, the area enclosed in the rectangle is indicative of the shear stress-time pairs obtained by operating in the speed ranges according to the present invention, i.e. between $10^{-4}$ and 10 m/s. In particular, by operating in conditions such as to remain below the area defined by the straight line τ=f(t) the integrity of the red blood cells is preserved. The shear stress/time pairs included in the rectangular area of FIG. 1 have been surprisingly shown to be such as to allow the loading of red blood cells without affecting their viability. Shear efforts between 1 and 500 Pa and time between 0.01 and 100 s have been shown to be capable of solving the technical problem according to the present invention. Even more preferably, the operating conditions fall under the straight line τ=f(t) of FIG. 1.

"Stress accumulation" is the parameter that allows sizing of the loading device and its operating parameters. To avoid hemolyzing red blood cells, SA must be lower than the mechanical hemolysis threshold defined, for example, by the aforementioned Tillman as $\tau^4 \cdot t = 10^7$ where T is the shear stress applied to the cell membrane and t is the time of application of the stress. The stress to which the red blood cells are exposed in the loading device according to the present invention is continuous, or, in a further embodiment, variable. In the embodiment with continuous stress, the red blood cells follow a path similar to a duct with a constant section and such as to expose them to a continuous and constant shear stress which allows the formation of temporary porosities on the membrane of the same. In the variable stress embodiment, the red blood cells cross a path similar to a duct with a variable section, said path allowing an SA such as to allow the formation of temporary porosities on the membrane of the same. A path similar to a duct means herein the path of the fluid in which the red blood cells are suspended inside the loading device according to the present invention, where at least part of said path takes place inside a microporous matrix and the section of the duct therefore corresponds to the size of the pores that the fluid passes through in the microporous matrix.

Said microfluidic methodology, operating with load losses of between 0.01 and 3 atm, never more than 5 atm, allows it to be operated in a macrofluidic circuit, said circuits being able to support the pressures necessary for the method itself. By way of example, the circuit typically used for dialysis is an example of a macrofluidic circuit.

The microporous matrix comprised in the loading device according to the present invention is housed in a suitable housing and is suitably sealed so that there is no leakage of blood between the microporous matrix and the housing itself. Thanks to the fact that the method according to the present invention operates at small pressures, no construction precautions or special materials are necessary to guarantee the seal, as it would instead be necessary to guarantee the seal if the method were to be applied at higher pressures. The solution, compared to state of the art solutions that need to work at high pressures, brings a significant constructive advantage.

It is a second object of the present invention a microporous matrix for implementing the method according to the present invention.

Said microporous matrix is characterized by pores having a minimum size that is at least 3 times the size of a red blood cell, that is, a minimum size of at least 20 µm; the pores in said microporous matrix have an average size, defined by parameters HC1, HC2 and WC1 and WC2, between 30 and 500 µm, or between 40 and 400 µm, or between 50 and 350 µm, or between 100 and 250 µm; said porous matrix has a length L of at least 1 mm, or at least 5 mm and a width W and a height H such as to comprise at least one unit cell. The volume of said microporous matrix is functional to create, within the same, one or more interconnected paths, wherein said at least one path is sufficiently long and with characteristics such as to expose the red blood cells suspended in the fluid that passes through it to a SA lower than the hemolysis threshold and sufficient to obtain an efficient loading. Said at least one path is the fluidic channel.

It is a further object of the present invention, with reference to FIG. 2A, a loading device 1 which comprises a microporous matrix 30 according to the present invention, suitably housed in a housing 35 which does not allow blood leakage between the porous medium and the housing itself, and an inlet port 36 and an outlet port 37. Optionally, said loading device also comprises a duct having a length and a section described by the dimensions w and h, wherein said length is comprised between 5 and 5000 mm, preferably between 5 and 500 mm, preferably between 40 and 200 mm, even more preferably between 40 and 130 mm, even more preferably of about 60 mm and where said section has dimensions related to the dimensions of the microporous matrix, without ever narrowing below 20 µm, where said duct has the function of connecting and/or transporting said suspension to/from said matrix. Said section has dimensions such that the smaller dimension between w and h of said section is greater than 20 µm, for example it is between about 20 µm and 5000 mm, or between about 20 µm and 500 mm, or between 20 µm and 50 mm, or between 20 µm and 5 mm, or between 20 µm and 500 µm, or between 30 µm and 200 µm. In a preferred embodiment, said section is constant along said duct, in alternative embodiments, said section varies along the duct, without however ever narrowing below 20 µm. In a further embodiment, said device comprises a first portion of a matrix connected to a second or further portion of a matrix via said duct.

Said loading device is made of polymeric material, and/or of ceramic material and/or of metallic material. In a further embodiment, it is a gel and/or a biological material.

Figure 6:
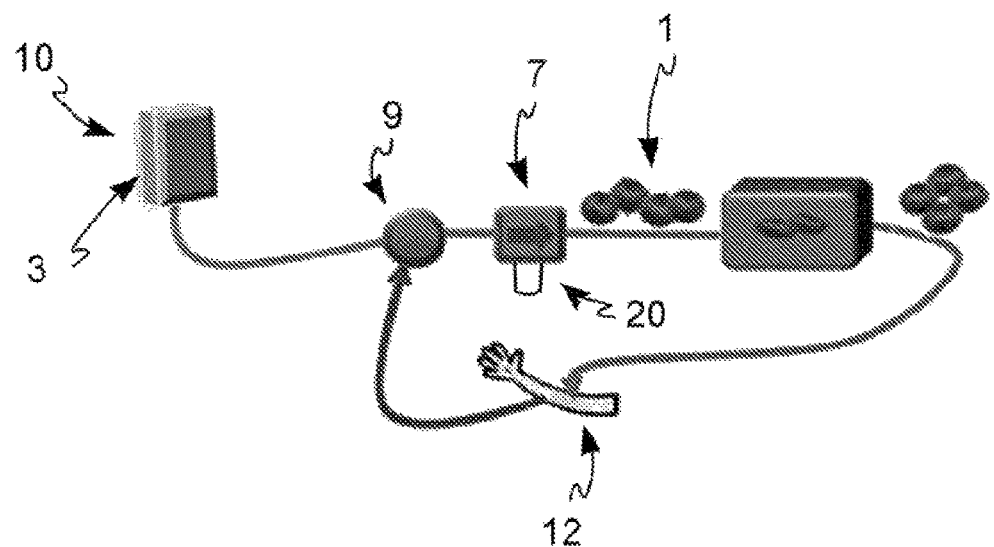
FIG. 6: schematic representation of a closed fluidic circuit.
Figure 7:
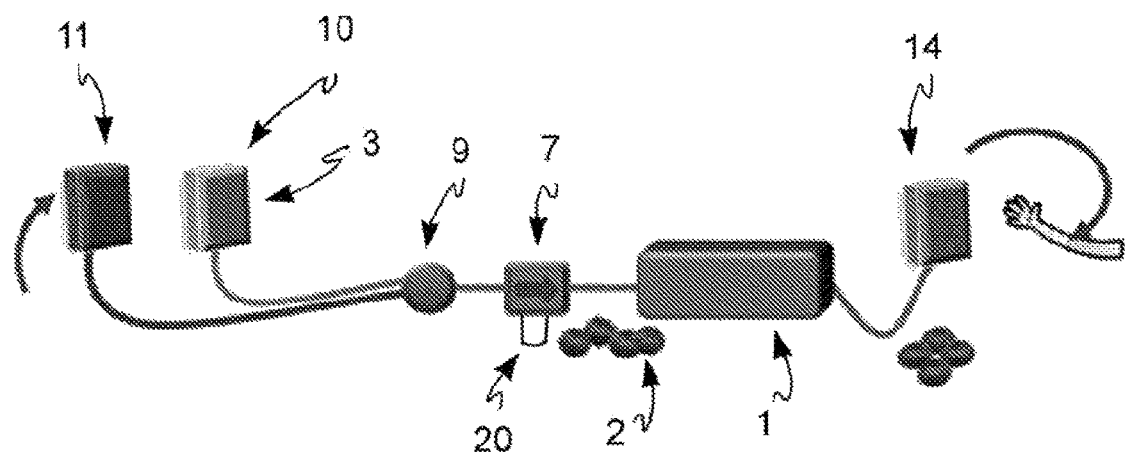
FIG. 7: schematic representation of an open fluidic circuit.

It is further object of the present invention a fluidic circuit for the implementation of the method according to the present invention. In one embodiment, said circuit is a closed fluidic circuit (FIG. 6). In a further embodiment, it is an open fluidic circuit (FIG. 7). Said circuit is fed with said at least one compound and with said red blood cells.

With reference to said FIGS. 6 and 7, said circuit comprises: a loading device 1, a pumping device 7, a mixer 9, a control system 20.

Said loading device 1 is a microfluidic device according to the present invention, which comprises at least one microporous matrix 30 and, optionally, a duct. In said microporous matrix, the pores have a minimum size that is at least 3 times the size of a red blood cell, i.e. a minimum size of at least 20 µm and an average size, defined by parameters HC1, HC2 and WC1 and WC2, between 30 and 500 µm, or between 40 and 400 µm, or between 50 and 350 µm, or between 100 and 250 µm. Said porous matrix has a length L of at least 1 mm, or at least 5 mm and a width W and a height H such as to comprise at least one unit cell. In a preferred embodiment, said microporous matrix has a length of between 5 and 1000 mm, preferably between 6 and 500 mm, or between 8 and 300 mm or between 100 and 200 mm. Preferably, said matrix has a height H equal to 2-1000 times, or 10-500 times, the height HU of the unit cell that makes it up and/or a width equal to 2-1000 times, or 10-500 times, the length LU of said unit cell. These pores generate within the said matrix at least one path which is a fluidic channel.

Before being inserted into said loading device 1, said red blood cells and said at least one compound pass through a mixer 9. The mixer is necessary where the flow generated in the fluidic circuit according to the present invention is a laminar flow, which therefore does not allow mixing of the suspension components. The mixer allows to improve the contact between the red blood cells and the at least one compound, so as to increase the loading efficiency.

In the embodiment with the open fluidic circuit, said mixer 9 receives said at least one compound 3 from a reservoir 10 and said red blood cells 2 from a bag 11. Said bag 11 contains whole blood, or a fraction of the whole blood which includes red blood cells or preferably red blood cells resuspended in PBS. In said embodiment, said suspension preferably comprises at least one anticoagulant and at least one preservative. In the embodiment with the closed fluidic circuit, said mixer 9 receives said at least one compound 3 from a reservoir 10 and said red blood cells 2 in suspension in the whole blood taken from the patient 12. In this embodiment, said at least one compound is preferably resuspended in PBS, so as to dilute said whole blood entering the mixer.

Said mixer, through said pumping device 7, introduces said suspension of at least a compound 3 and red blood cells 2 into said loading device 1.

Inside said loading device, said mixture is distributed in said at least one microporous matrix and loading takes place of said at least one compound 3 into said red blood cells 2. In the open circuit embodiment, the red blood cells thus processed emerge from said loading device 1 and are collected in an encapsulated blood bag 14.

In the closed circuit embodiment, said encapsulated blood is re-infused into the patient 12.

Said pumping device 7 is selected, for example, from a syringe pump, a peristaltic pump, a centrifugal pump.

Said pumping device 7 is controlled by said control system 20 and said control system 20 forces in said at least one microporous matrix comprised in said loading device 1 an average flow speed comprised between $10^{-4}$ and 10 m/s.

Figure 5:
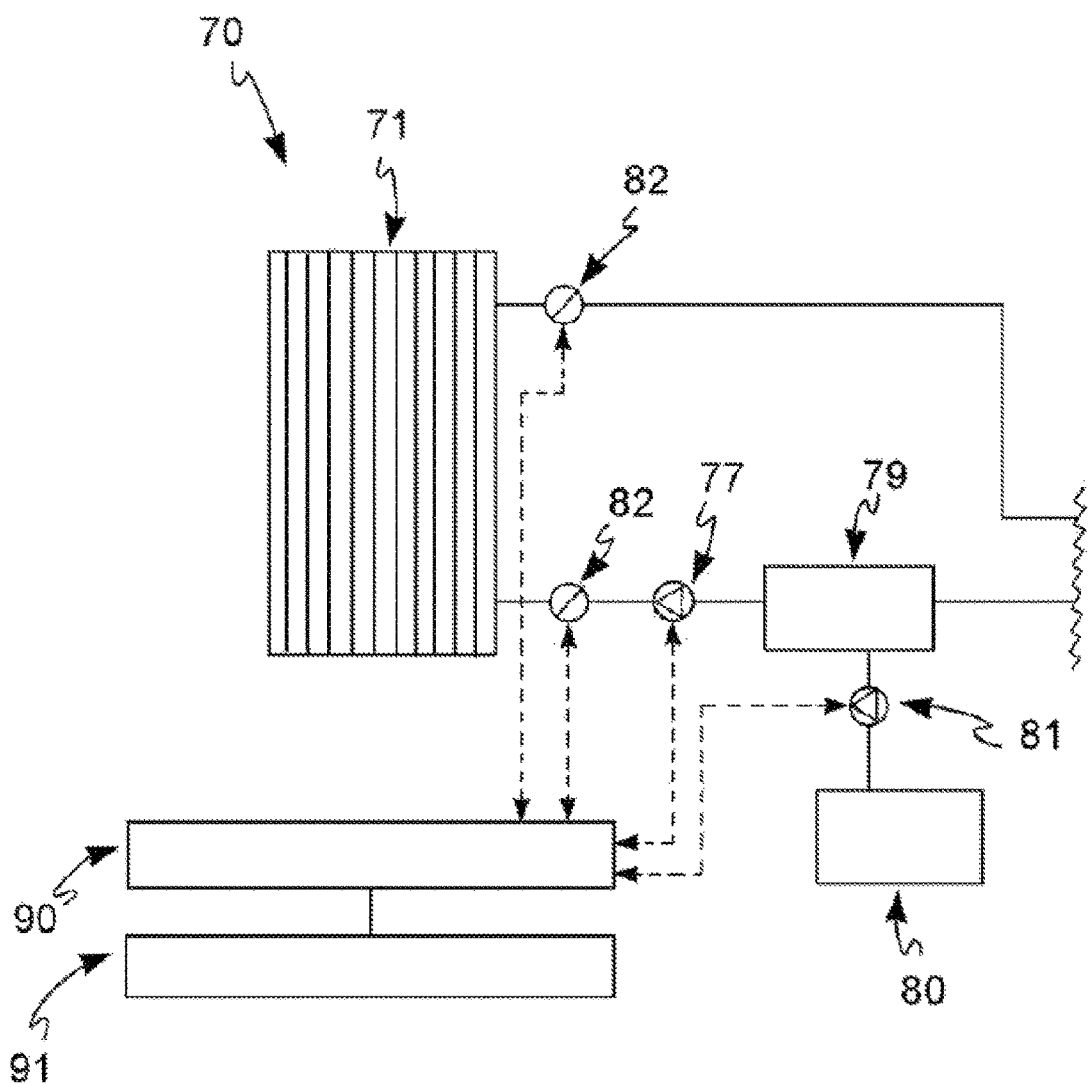
FIG. 5: schematic representation of the machine according to an embodiment.

In a further aspect, it is an object of the present invention a machine 70 for extracorporeal treatment of blood comprising, with reference to the scheme of FIG. 5:
- a loading device 71;
- at least a pumping device 77 for creating an extracorporeal hematic flow between a subject or a blood bag and the loading device 71;
- at least a reservoir 80 containing at least one compound to be loaded in said blood;
- at least a mixer 79 for mixing said blood with said at least one compound;
- optionally, at least a pump 81 for entering in said mixer 79 said at least one compound from said reservoir 80;
- sensors 82 for controlling chemical physical parameters of the blood suspension before and/or after it passes through said loading device;

a control device 90 for adjusting a blood flow value depending on the target blood flow value, wherein the control device 90 comprises:

a control/regulation unit for adjusting the current blood flow to the predetermined or selected flow;

optionally, a control/regulation unit for defining the amount of said at least one compound to be entered in said mixer 79 from said at least on reservoir 80;

an electronic communication unit 91 which is useful for the user, on the one hand, to visualize, and on the other, to input the treatment parameters corresponding to the parameters of the blood treatment machine, such as the blood flow, the amount of said at least one compound to be mixed, chemical-physical parameters of the suspension before and/or after passing through said loading device 71. This is done for example via a graphical interface of the machine.

Said machine receives blood from a blood pump that extracts blood from a subject's body through an access to the patient, or from a bag that contains whole blood or a fraction thereof, preferably a fraction of whole blood which includes red blood cells, more preferably a suspension of red blood cells.

Said loading device 71 is a microfluidic device which comprises at least one microporous matrix and, optionally, a duct, as defined above. In said microporous matrix, the pores in said microporous matrix have a minimum size which is at least 3 times the size of a red blood cell, i.e. a minimum size of at least 20 μm; said pores have an average size, defined by parameters HC1, HC2 and WC1 and WC2, between 30 and 500 μm, or between 40 and 400 μm, or between 50 and 350 μm, or between 100 and 250 μm and said microporous matrix has a length L of at least 1 mm, or at least 5 mm and a width and height such as to comprise at least one unit cell. In a preferred embodiment, said microporous matrix has a length of between 5 and 1000 mm, preferably between 6 and 500 mm, or between 8 and 300 mm or between 100 and 200 mm. Preferably, said matrix has a height equal to 2-1000 times, or 10-500 times, the height HU of the unit cell that composes it and/or a width equal to 2-1000 times, or 10-500 times, the width WU of the same unit cell.

Said control unit 90 regulates the flow rate in each of said microchannels comprised in said loading device so as to have an average speed comprised between $10^4$ and 10 m/s The red blood cells loaded in accordance with the present invention find application in clinical practice or in experimental research. By way of example, said compounds can be DNA, RNA, monoclonal antibodies, inorganic molecules, organic molecules used for therapeutic purposes, for example in the treatment of tumors or for diagnostic purposes, for example to perform an intracellular labelling.

The method according to the present invention offers a series of advantages compared to what is available in the state of the art.

The loading of red blood cells is mediated by fluid dynamics and diffusion phenomena. The effect obtained is that of a temporary opening of some of the pores present on the cell membrane of the red blood cells which allows entry into the same by diffusion of the compound(s) present in the solution in which the red blood cells are found, operating in sub-hemolytic conditions.

Surprisingly, the method, thanks to the identification of a combination of shear stresses/stress times, induces the passage of the compound(s) inside the cell without causing any permanent alteration to the physiological state of the membrane. In fact, the porosities are not distributed homogeneously on the red blood cell membrane but are localized exclusively in the regions characterized by specific shear stresses.

The method according to the present invention also allows avoiding forced contacts with external materials (surfaces of devices, different fluids such as isotonic/hypertonic fluids to be used for the loading of cells with compounds based on osmosis).

The following examples are intended to better clarify the invention, are not to be considered in any way limiting the scope of protection.

Example 1: Loading Device with a Microporous Matrix

FIG. 2 shows a schematic representation of a loading device with a porous matrix according to one embodiment.

Figure 2B:
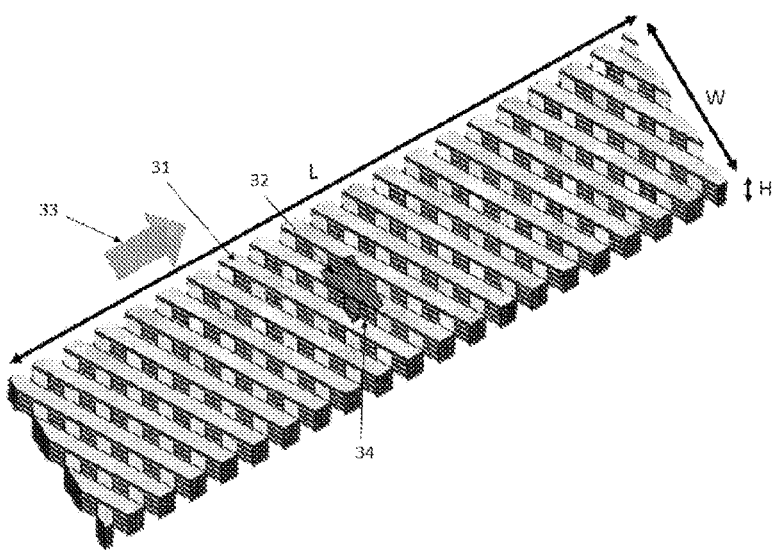
Figure 2C:
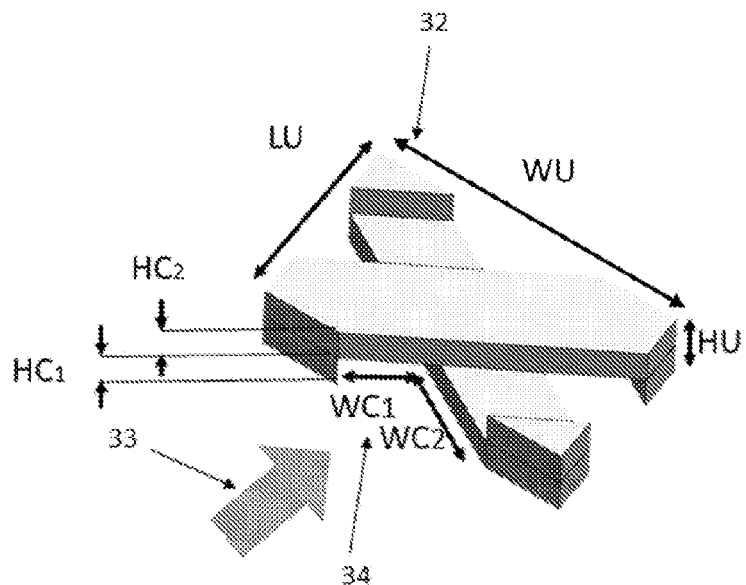
Figure 2D:
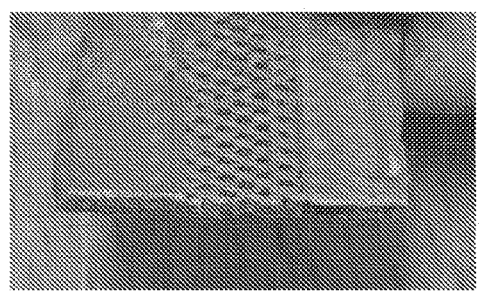

The porous matrix, which in one embodiment is schematically represented in FIG. 2B, was printed with 3D printing in PLA (polylactic acid). In the embodiment of FIG. 2, panel A shows a prospective image of the loading device, and panel B an enlarged prospective schematic representation of a portion 31 of said microporous matrix 30. In the enlargement, the length L, in the direction of the flow 33, the overall height H and the overall width W are highlighted. Said microporous matrix consists of a repetition of unit cells 32. In FIG. 2C, an enlarged unit cell 32 is schematized. Said unit cell 32 is crossed by a flow in the direction of the arrow 33 and has a length LU in the direction of the flow, a thickness HU and forms a fluidic channel 34. Said fluidic channel 34, inside said unit cell 32 ha a height which in two different sections is HC1 or HC2, and widths WC1 or WC2 inside the unit cell. Said thicknesses HC1 and HC2 are the same or different from each other. Said widths WC1 and WC2 are the same or different from each other. The repetition in the space of a unit cell 32 originates the entire microporous matrix 30

In the embodiment of the example, said microporous matrix 30 has homogeneous porosities, wherein the pore dimensions are equal to 50 μm×400 μm, that is HC1 is equal to HC2 and is equal to 50 μm, WC1 is equal to WC2 and measure 400 μm. The total height of the matrix H is 1.5 mm, the total width W is 3 mm, the length L is 50 mm.

Said microporous matrix is suitably housed in a housing that does not allow blood to leak between the porous medium and the housing itself. Said microporous matrix is open to the outside by an inlet port 36 and an outlet port 37 located at the two longitudinal ends of said microporous matrix.

Example 2: Encapsulation Efficiency

The loading tests were carried out on the microporous matrix of example 1 with bovine blood with hematocrit Ht=10%, with flow rates up to 1.3 ml/min with stress times up to 0.9 s, with SA value estimated around $Pa^4$ s, calculated with Tillman formula.

Figure 4A:
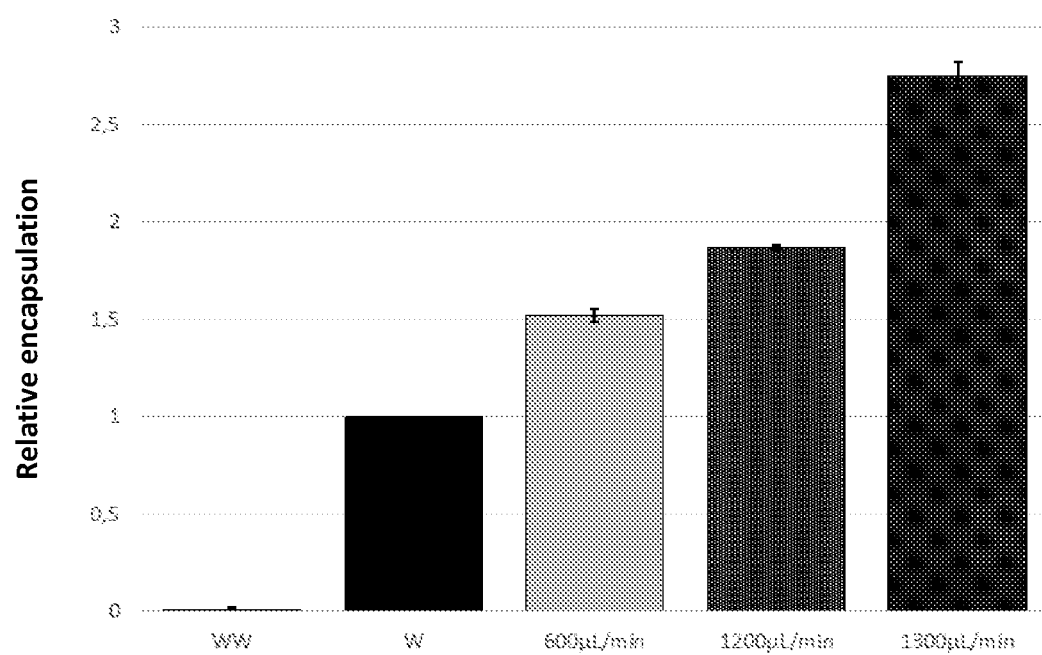
FIG. 4: fluorescence observed in bovine blood samples (panels A, B, C) or human blood samples (panels D, E): (A) samples loaded with dextran at defined concentration and increasing flow rates, relative encapsulation in a loading device comprising a microporous matrix according to the present invention, with a fluidic channel characterized by minimum sections 50 µm*400 µm; (B) samples loaded with dextran at defined concentration and increasing flow rates, relative encapsulation in a duct having constant section 50 µm*50 µm (comparative); (C) samples loaded with dextran at defined concentration and increasing flow rates, relative encapsulation in a duct having constant section 100 µm*100 µm (comparative); (D) suspension of human erythrocytes with hematocrit Ht=10%, samples loaded with dextran at defined concentration and increasing flow rates, in a loading device comprising a microporous matrix according to the present invention, with a fluidic channel characterized by minimum sections 50 µm*400 µm; (E) suspension of human erythrocytes with hematocrit Ht=10%, samples loaded with doxorubicin at increasing flow rates in a loading device comprising a microporous matrix according to the present invention, with a fluidic channel characterized by minimum sections 50 µm*400 µm.

The geometry of the microporous matrix implies a variable stress for the red blood cells that are to cross a path with a section equal to 50 μm and then move on to sections with a larger section. The stress obtained with the geometry tested here is in the range from 1 Pa to 10 Pa. FIG. 4A shows the encapsulation percentages obtained as an increase in the fluorescence of the FITC-dextran probe molecule 40 kDa (dextran with molecular weight of 40 kDa labelled with a fluorophore) compared to the control. As control (blank), both the same suspension of red blood cells to which dextran was not added (WW), and the same suspension of red blood cells with dextran (diffusive control, W) was used but not inserted in the loading device, thus not solicited fluid-dynamically. After passing into the microporous matrix, 100 µl of the processed solution was resuspended in PBS, washed and centrifuged to remove the excess dextran left in solution or attached to the outer membrane of the red blood cells and then the encapsulation of dextran was measured by fluorescence measurement.

The samples were analyzed with a spectrophotometer to verify the fluorescence intensity. Fluorescence is assessed by measuring the fluorescence intensity of a constant amount of red blood cells, separated from the solution in which the loading took place and lysed in distilled water in order to put in solution what is inside the cells.

To evaluate the process efficiency, the sample fluorescence is calculated by comparing it with an untreated sample (control, corresponding to the diffusive control), taken as a reference The graph shows a blood flow dependent increase in the encapsulation values.

It should be noted that, by using the microporous matrix object of the present invention, a high loading efficiency is obtained, reaching 275% compared to the diffusive control, with flow rates of 1300 µl/min. The flow rates, and therefore the volumes of blood that the method according to the present invention makes possible to treat, are compatible for clinical use. With a 1.5 mm*3 mm*50 mm microporous matrix, an efficient loading of about 60 ml of blood in one hour has in fact been demonstrated. The size of the matrix can be suitably increased, thus allowing to treat larger blood volumes in the unit of time. As an example, the method according to the present invention allows an efficient loading of a volume of 500 ml of blood in an hour.

Figure 4B:
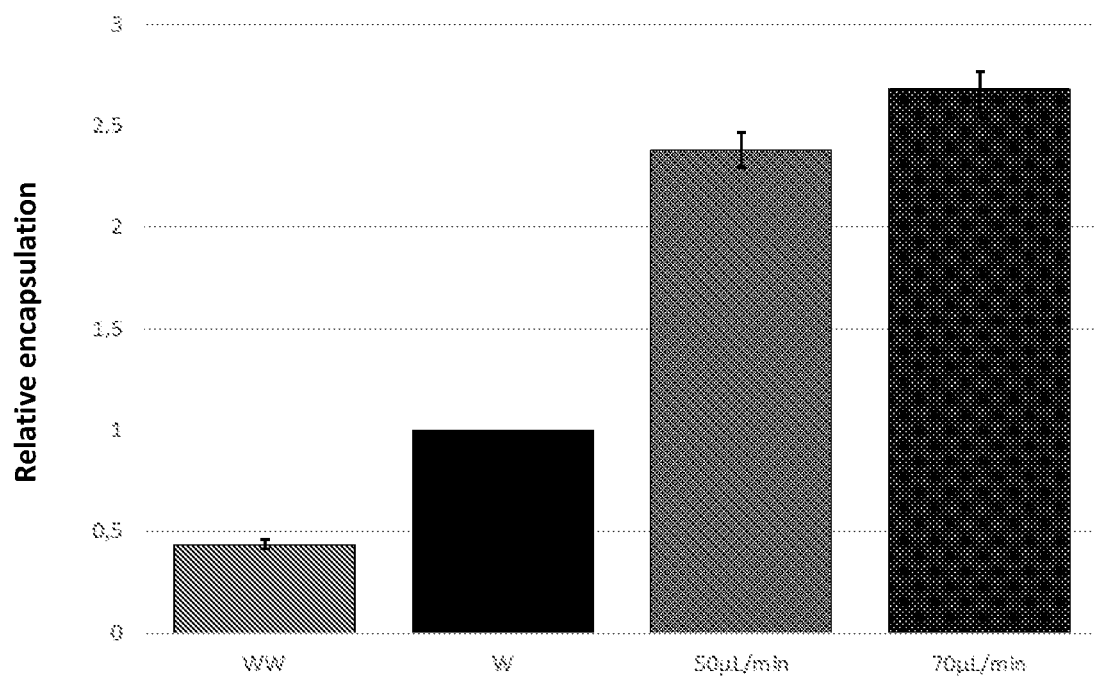

For comparative purposes, a loading test was carried out again with bovine blood at 10% of hematocrit, using a loading device consisting of a duct with a constant section of 50 µm*50 µm. The stress times were up to 2 s, with estimated SA values of the order of $10^5$ $Pa^4$ s. In this device, the stress is constant, of the order of 10 Pa. FIG. 4B shows the percentages of encapsulation obtained as an increase in the fluorescence of the FITC-dextran 40 kDa probe molecule compared to the controls, as described above. The device leads to an encapsulation with lower efficiency and with significantly lower flow rates, where, by continuing the procedure for about an hour, it would be possible to treat only 4 ml.

Figure 4C:
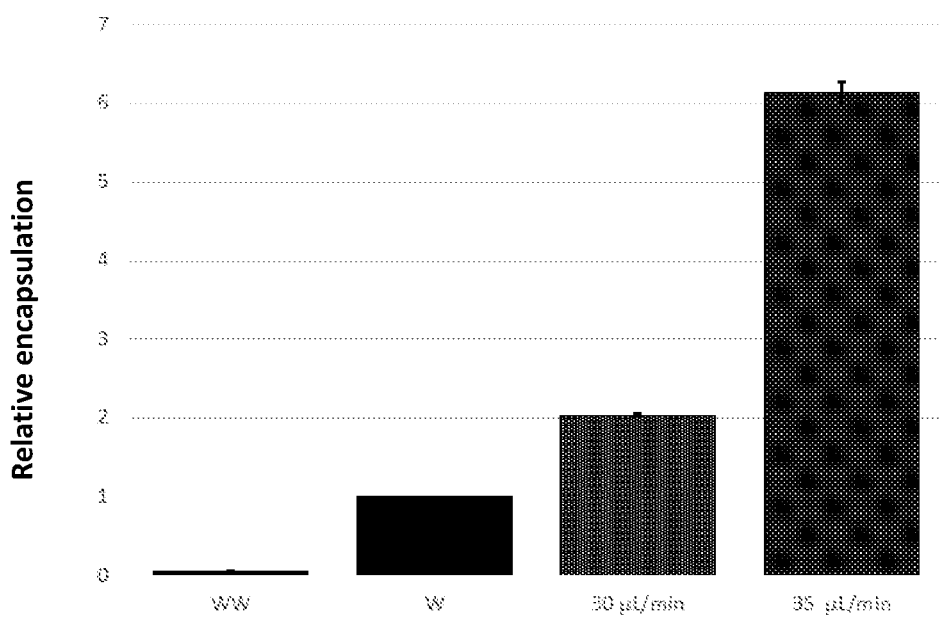
Figure 4D:
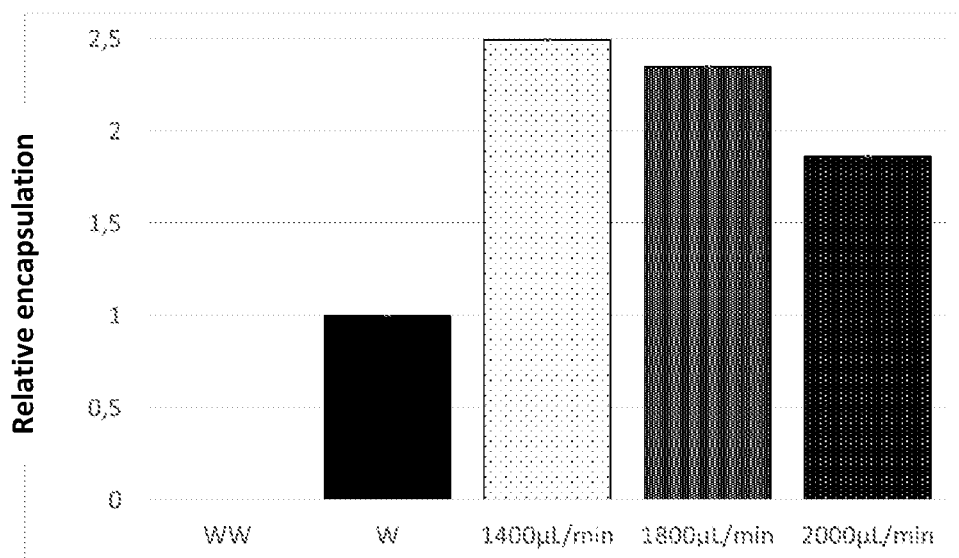

A further experiment was carried out using a loading device consisting of a duct with a constant section of 100 µm*100 µm. In this case, the experiment was conducted on bovine whole blood. The stress times were up to 1 s, with estimated SA values of the order of $10^5$ $Pa^4$ s. In this device, the stress is constant, of the order of 10 Pa. FIG. 4C shows the encapsulation percentages obtained as an increase in the fluorescence of the probe molecule FITC-dextran 40 kDa compared to the controls, as described above. The device leads to an encapsulation with an efficiency about three times that obtained with the microporous matrix according to the present invention but with much lower flow rates, not compatible with clinical applications. By continuing the procedure for about an hour, it would be possible to treat only a volume of about 4 ml. It is important to note that the loading efficiency, in the experiment shown in FIG. 4C, is higher than that observed in the previous experiment, which although took place in a duct with a constant and lower section. The increase in efficiency is obtained here because it is done with whole blood, and not with a suspension of red blood cells. Whole blood, having a higher viscosity, increases SA improving the encapsulation efficiency. As shown by the following data (FIG. 4D), a comparable efficiency improvement is obtained in the microporous matrix according to the present invention, also by having a human blood flow. After optimizing the loading procedure, the encapsulation efficiency of the FITC-dextran 40 KDa probe molecule was tested in a suspension of human erythrocytes with hematocrit Ht=10%, at flow rates up to 2 ml/min. The loading tests were carried out on the same microporous matrix as in example 1.

The fluorescence intensity, proportional to the efficiency of the loading in the different flow rates considered, was measured by flow cytometer. Also in this analysis, the increase in fluorescence intensity was expressed in relation to the value measured in the same population of erythrocytes of the diffusive control. To confirm the result, the spectrophotometric analysis performed as for the tests with bovine erythrocytes was also repeated (FIG. 4C). Both analyzes demonstrated an increase dependent on blood flow values in the encapsulation values.

It should be noted that, by using the microporous matrix object of the present invention, loading efficiency up to 10 times higher than with diffusive control is obtained, with flow rates of 2000 µl/min.

In order to test the applicability of the erythrocyte loading system by means of a microporous matrix in clinical practice, the experiments were repeated using a small chemotherapy drug with a molecular weight of less than 1 kDa as the probe molecule. Doxorubicin was used.

Figure 4E:
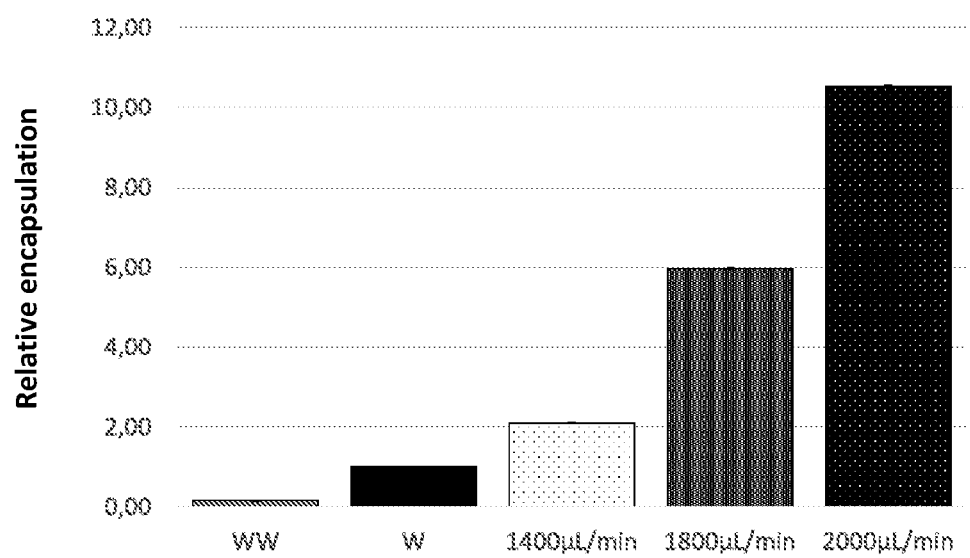

FIG. 4E shows that the microfluidic solicitation of human erythrocytes by means of a microporous matrix according to the present invention entails the efficient encapsulation of small molecules, obtaining an encapsulation that is more than double compared to the diffusive control only at flow rates compatible with the current intravenous administration times of such therapies.

Example 3: Cell Morphology Analysis after Encapsulation

Figure 3:
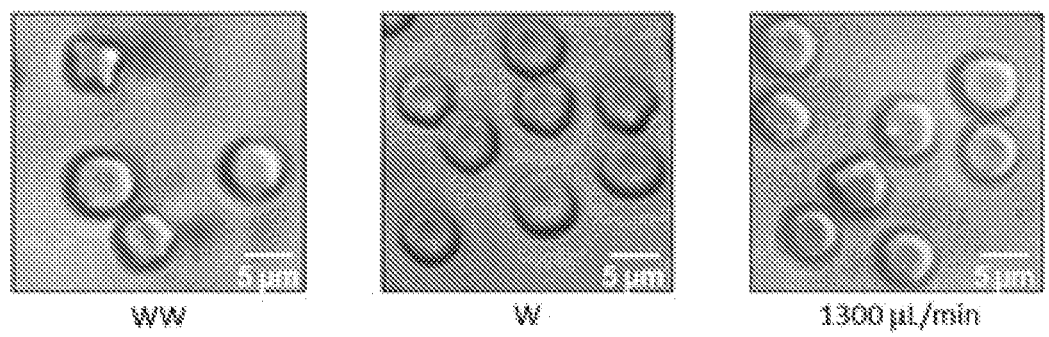
FIG. 3: images acquired through an optical microscope (magnification 40×) of red blood cells encapsulated according to the methodology of the present invention. The images show that the red blood cells are not subjected to excessive deformation when microfluidically strained in the device according to the present invention (the example shows the sample stressed to flow rates equal to 1300 µl/min) and are not damaged by the presence of encapsulated dextran. WW=red blood cell suspension without addition of dextran. W=same red blood cell suspension with addition of dextran (diffusive control). 1300 µl/min=red blood cell after being exposed to dextran according to the methodology of the present invention.

FIG. 3 shows the results obtained after processing the red blood cells, compared with the reference, wherein the processing is carried out by having the suspension of red blood cells pass through a microporous matrix according to the present invention at a flow rate of 1300 µl/min. The images show that the red blood cells do not undergo excessive deformation when microfluidically stressed in the device according to the present invention (the example shows the stressed sample at flow rates equal to 1300 µl/min) and are not damaged by the presence of the encapsulated dextran.

The processed cells were viewed under an optical microscope. The red blood cells retain the biconcave disc shape.

The invention claimed is:

1. A method to introduce compounds inside red blood cells, the method comprising:
providing red blood cells from a subject;
providing one or more compounds to be encapsulated in the red blood cells;
providing a loading device comprising a microporous matrix;
feeding the loading device with a suspension comprising the red blood cells and the one or more compounds; and
collecting the red blood cells exiting from the loading device, which are encapsulated red blood cells;
wherein:
the red blood cells and the one or more compound are in suspension at a pH of between 6.8 and 7.8;

the pores in the microporous matrix have a minimum size of at least 3 times the size of a red blood cell, that is a minimum size of at least 20 μm;

the pores in the microporous matrix have an average size of between 30 and 500 μm;

the porous matrix has a length L of at least 1 mm and a width W and a height H such that it comprises at least one unit cell, the unit cell being equal to the microporous matrix volume that, repeated by rototranslation through the vectors that generate the matrix, fills the whole matrix itself, and wherein the loading device is fed with the suspension in such a way to obtain an average fluid speed of between $10^{-4}$ and 10 m/s.

2. The method according to claim 1, wherein the pores in the microporous matrix have an average size of between 40 and 400 μm.

3. The method according to claim 1, wherein the pores in the microporous matrix have an average size of between 50 and 350 μm.

4. The method according to claim 1, wherein the pores in the microporous matrix have an average size of between 100 and 250 μm.

5. The method according to claim 1, wherein the loading device further comprises at least one duct having a length parallel to a main direction of the flow of the suspension in the channel and a section, described by dimensions w ×h, transversal to the flow itself, wherein the section has dimensions such that a smaller dimension between w and h of the section is greater than 20 μm.

6. The method according to claim 1, wherein the red blood cells are suspended in PBS, or the red blood cells are suspended in whole blood and a hematocrit of the suspension is of between 1 and 50%.

7. The method according to claim 6, wherein the red blood cells are suspended in albumin supplemented PBS.

8. Red blood cells encapsulated with at least one compound according to the method of claim 1.

9. Encapsulated red blood cells according to claim 8 for use in the treatment of diseases.

* * * * *